US012768813B2

(12) United States Patent
Branciforte et al.

(10) Patent No.: US 12,768,813 B2
(45) Date of Patent: Oct. 20, 2026

(54) SOIL MOISTURE SENSOR BASED ON ELECTROSTATIC SENSING

(71) Applicant: STMicroelectronics International N.V., Geneva (CH)

(72) Inventors: Marco Maria Branciforte, Catania (IT); Fabrizio La Rosa, San Pietro Clarenza (IT)

(73) Assignee: STMicroelectronics International N.V., Geneva (CH)

( * ) Notice: Subject to any disclaimer, the term of this patent is extended or adjusted under 35 U.S.C. 154(b) by 314 days.

(21) Appl. No.: 18/457,143

(22) Filed: Aug. 28, 2023

(65) Prior Publication Data

US 2025/0076249 A1 Mar. 6, 2025

(51) Int. Cl.

| | |
|---|---|
| ***G01N 27/60*** | (2006.01) |
| ***G01N 33/24*** | (2006.01) |

(52) U.S. Cl.

CPC ........... *G01N 27/605* (2013.01); *G01N 33/24* (2013.01); *G01N 33/245* (2024.05)

(58) Field of Classification Search

CPC ..... G01N 33/245; G01N 33/24; G01N 27/605

See application file for complete search history.

(56) References Cited

U.S. PATENT DOCUMENTS

| | | | | |
|---|---|---|---|---|
| 5,424,649 A * | 6/1995 | Gluck .................. | G01N 27/223 324/690 |
| 8,981,946 B2 * | 3/2015 | Runge .................. | A01G 25/167 700/282 |
| 2010/0277185 A1 * | 11/2010 | Hughes ................ | G01N 33/246 324/664 |

(Continued)

FOREIGN PATENT DOCUMENTS

| | | | |
|---|---|---|---|
| CN | 114088769 | A | 2/2022 |
| EP | 3791787 | A1 | 3/2021 |
| KR | 20190102446 | A | 9/2019 |

OTHER PUBLICATIONS

"Build DIY Soil Moisture Meter Using Arduino Nano," NextPCB, Jan. 12, 2023, 6 pages, © CC BY-SA.

Adla, S. et al., "Laboratory Calibration and Performance Evaluation of Low-Cost Capacitive and Very Low-Cost Resistive Soil Moisture Sensors," Sensors 2020, 20, 363, MDPI, Jan. 8, 2020, 27 pages.

(Continued)

*Primary Examiner* — Lee E Rodak
*Assistant Examiner* — Taqi R Nasir
(74) *Attorney, Agent, or Firm* — Slater Matsil, LLP

(57) ABSTRACT

A soil sensor includes a signal generator, and a transmitter coupled to the signal generator, the transmitter configured to transmit a signal from the signal generator, the signal having a fixed frequency, the transmitter including a transmit electrode embedded within a first dielectric material. The soil sensor includes a receiver, the receiver being configured to electrostatically couple to the transmitter through a channel including soil, the receiver including a charge variation (QVAR) electrode embedded within a second dielectric material. The soil sensor includes a charge variation (QVAR) sensor coupled to the QVAR electrode, the QVAR sensor configured to detect a variation in charge detected at the QVAR electrode in response to the signal from the signal generator and output a digital signal including the charge detected. And the soil sensor further includes a processing circuit coupled to the QVAR sensor and configured to determine a level of moisture in the channel based on the digital signal.

20 Claims, 9 Drawing Sheets

(56) References Cited

U.S. PATENT DOCUMENTS

| | | | | |
|---|---|---|---|---|
| 2015/0330932 | A1* | 11/2015 | Kumaran ............ | G01N 27/223<br>324/664 |
| 2016/0223450 | A1* | 8/2016 | Gimenez Calbo ..... | G01N 13/02 |
| 2020/0110170 | A1* | 4/2020 | Chandra ............. | G01N 27/048 |
| 2021/0081032 | A1 | 3/2021 | Passaniti et al. | |
| 2023/0019962 | A1 | 1/2023 | Guarnera et al. | |

OTHER PUBLICATIONS

Hrisko, J., "Capacitive Soil Moisture Sensor Theory, Calibration, and Testing," Maker Portal LLC, Jul. 5, 2020, 12 pages, New York, NY.

Yu, L. et al., "Review of research progress on soil moisture sensor technology," Int. J. Agr. & Biol. Eng., Open Access at https://www.ijabe.org, vol. 14, No. 4, Jul. 2021, 11 pages.

* cited by examiner

SOIL MOISTURE SENSOR BASED ON ELECTROSTATIC SENSING

TECHNICAL FIELD

The present invention relates generally to soil moisture sensing, and in particular embodiments, to soil moisture sensors based on electrostatic sensing.

BACKGROUND

Soil moisture sensing plays a crucial role in optimizing irrigation practices, managing crop health, and conserving water resources. Over time, many electronic soil moisture sensors have been developed, employing various principles such as resistive, capacitive, or time domain reflectometry (TDR) to measure the moisture level of a patch of soil.

Resistive soil moisture sensors operate based on the principle that the electrical resistance of the soil changes with moisture content. While these sensors are relatively simple and inexpensive, they are susceptible to interference from soil salinity, temperature, and electrical conductivity variations, resulting in reduced accuracy and reliability. Typical soil moisture sensors' electrodes make direct contact with soil, and as a result, corrode due to water exposure.

Capacitive soil moisture sensors utilize the dielectric properties of the soil, which vary with moisture content, to estimate soil moisture levels. These sensors measure the capacitance between electrodes embedded in the soil. While capacitive sensors offer improved accuracy and reduced sensitivity to soil salinity compared to resistive sensors, they still face challenges in accurately determining soil moisture levels under different soil types and environmental conditions.

Time domain reflectometry (TDR) sensors emit an electromagnetic pulse into the soil and measure the time it takes for the pulse to reflect back. This measurement is correlated with the soil's dielectric constant, which in turn is related to soil moisture content. TDR sensors provide accurate and reliable soil moisture measurements but are relatively expensive and may require complex calibration procedures.

Traditional methods of soil moisture measurement, such as gravimetric techniques and tensiometers, have limitations in terms of labor-intensiveness, limited spatial coverage, and inability to provide real-time data. Current sensors are expensive to purchase and costly to maintain (due to the sensor operating in a wet environment).

SUMMARY

In accordance with an embodiment of the present invention, a soil sensor includes a signal generator. The soil sensor further includes a transmitter coupled to the signal generator, the transmitter configured to transmit a signal from the signal generator, the signal having a fixed frequency, the transmitter including a transmit electrode embedded within a first dielectric material. The soil sensor further includes a receiver, the receiver being configured to electrostatically couple to the transmitter through a channel including soil, the receiver including a charge variation (QVAR) electrode embedded within a second dielectric material. The soil sensor further includes a charge variation (QVAR) sensor coupled to the QVAR electrode, the QVAR sensor configured to detect a variation in charge detected at the QVAR electrode in response to the signal from the signal generator and output a digital signal including the charge detected. And the soil sensor further includes a processing circuit coupled to the QVAR sensor and configured to determine a level of moisture in the channel based on the digital signal.

An embodiment soil moisture detection method includes having a transmitter and a receiver of a soil sensor in a patch of soil. The soil moisture detection method further includes transmitting an output signal from a signal generator through the transmitter. The soil moisture detection method further includes detecting the output signal at the receiver. The soil moisture detection method further includes sensing the detected output signal at a charge variation (QVAR) sensor as QVAR signal. And the soil moisture detection method further includes processing the digital signal from the QVAR sensor to obtain a moisture content of the patch of soil.

An embodiment soil sensor calibration method includes placing a transmitter and a receiver of a soil sensor in a first patch of soil. The soil sensor calibration method further includes generating a first soil moisture measurement using the soil sensor. The soil sensor calibration method further includes after generating the first soil moisture measurement, adding a known volume of water to the patch of soil. The soil sensor calibration method further includes after adding the water, generating a second soil moisture measurement using the soil sensor. And the soil sensor calibration method further includes determining a moisture content calibration table for the soil based on the first and the second moisture measurements.

BRIEF DESCRIPTION OF THE DRAWINGS

For a more complete understanding of the present invention, and the advantages thereof, reference is now made to the following descriptions taken in conjunction with the accompanying drawings, in which.

DETAILED DESCRIPTION OF ILLUSTRATIVE EMBODIMENTS

Figure 1:
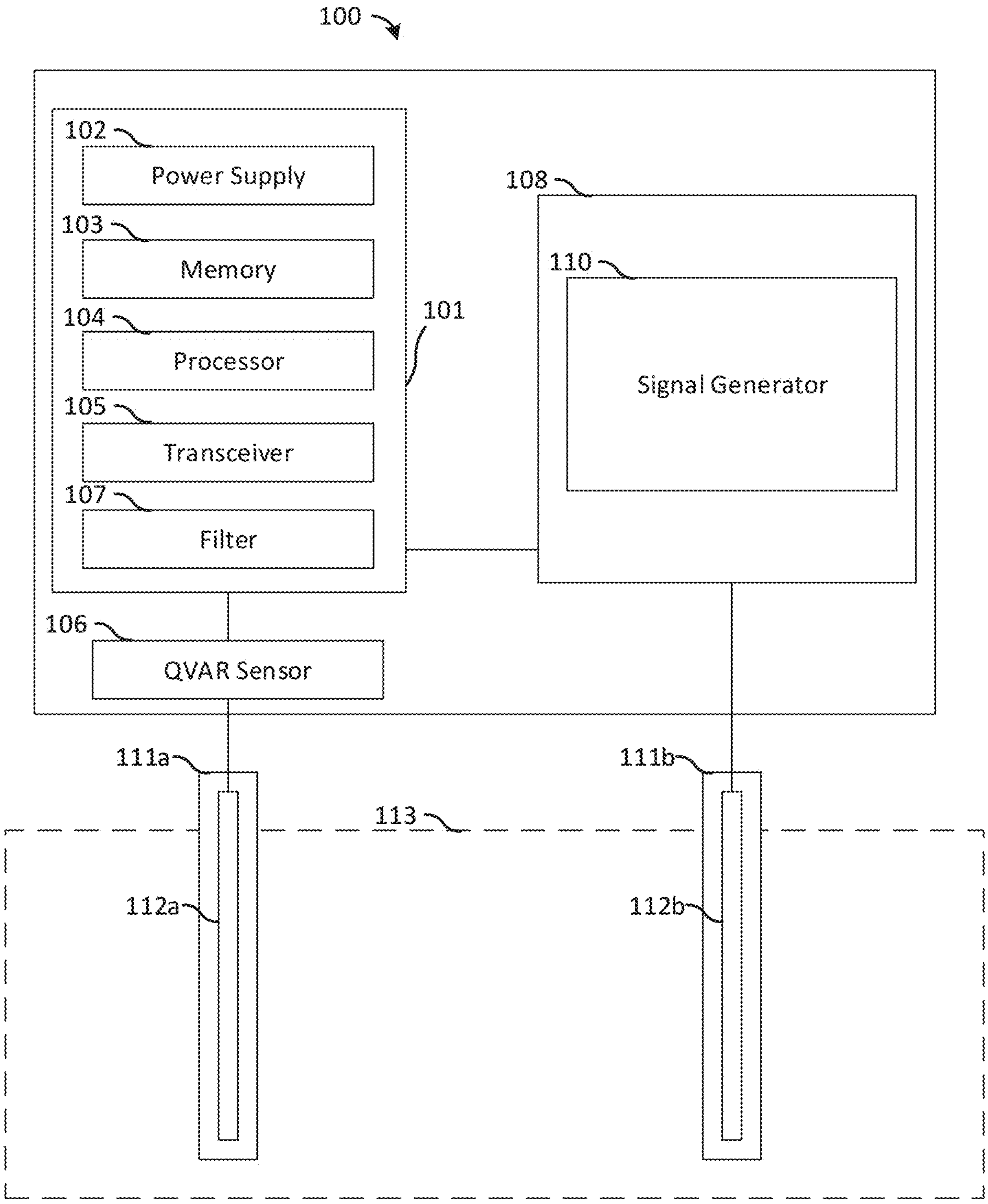
FIG. 1 is a component schematic diagram of an electronic device in accordance with some embodiments.

A soil sensor detects and monitors moisture levels of soil. Over time, soil sensors have become a necessary tool for those in the agricultural and farming industries to improve the efficiency of their operations. Soil sensors provide these industries with accurate, real-time data on soil conditions, leading to improved decision-making, resource optimization, and increased productivity. In particular, soil sensors help farmers optimize their irrigation practices by providing real-time data on soil moisture levels. This information allows farmers to determine the exact amount and timing of water required by their crops, thus minimizing water wastage and reducing the risk of over- or under-irrigation.

Several types of soil sensors that detect moisture levels are available in the market, each employing different technologies to measure the soil moisture content. A few commonly used soil sensor types for moisture detection include: capacitance sensors, tensiometers, time domain reflectometry (TDR) sensors, frequency domain reflectometry (FDR) sensors, and resistive sensors.

Capacitance sensors measure soil moisture by evaluating the electrical capacitance between two or more electrodes inserted into the soil. The moisture content affects the dielectric constant of the soil, which, in turn, alters the capacitance. By measuring this change, capacitance sensors estimate the moisture level in the soil.

Tensiometers measure soil moisture tension, also known as soil water potential. These sensors consist of a porous ceramic cup that is filled with water. As the soil dries, water is drawn out of the cup, creating a negative pressure. The tension in the water is measured using a pressure gauge, providing an indication of the soil moisture status.

Time domain reflectometry (TDR) sensors determine soil moisture by measuring the propagation time of electromagnetic pulses through the soil. These sensors have two electrodes inserted into the soil, and a pulse of electromagnetic energy is sent between them. The time taken for the pulse to travel reflects the soil's dielectric properties, which correlate with moisture content.

Frequency domain reflectometry (FDR) sensors analyze the dielectric properties of the soil to estimate moisture levels. These sensors emit electromagnetic waves at different frequencies and measure the reflected signals. The frequency at which the reflected signal changes indicates the soil moisture content.

Resistive sensors consist of a porous block that absorbs and releases moisture based on soil conditions. The resistance of the block changes with moisture content, and this change is used to estimate soil moisture levels.

All of the above sensors can be connected to data loggers or integrated into automated irrigation systems, allowing farmers to monitor soil moisture levels and make informed decisions about irrigation scheduling and water management practices.

Though soil sensors are exceedingly useful, current sensors are expensive to purchase and costly to maintain (due to the sensor operating in a wet environment). There is a need for innovation to bring the cost of the soil sensors down, as well as a need to improve the robustness of the sensors. An efficient and robust system and method that provides protection from the environment and reduces cost of the soil moisture sensor is desirable.

In various embodiments, the soil sensor of this disclosure incorporates an electrostatic sensor to measure the soil moisture content of a patch of soil, which is different from techniques currently employed (such as capacitive or resistive techniques). Embodiments of this disclosure describe a new class of electrostatic soil sensor for moisture detection. In an embodiment, this disclosure uses a new type of electrostatic sensor called a charge variation (QVAR) sensor. Aspects of this disclosure include a QVAR sensor coupled with a passive electrode. Although the QVAR sensor has a single differential input that comprises two input pins (which may be coupled to two or more electrodes), this disclosure details the case of only using a single input pin of the differential input and leaving the remaining input pin floating.

In embodiments, a variation in an electric field near the active (receiver or QVAR) electrode of the QVAR sensor induces a charge polarization on the active electrode. This charge polarization equates to a voltage that is proportional to the variation in electric field. To generate a changing electric field near the receiver electrode connected to the QVAR sensor, a signal generator is connected to a transmitter electrode, and the transmitter electrode is placed a fixed distance from the receiver electrode. In an embodiment, the signal generator generates a signal with a fixed amplitude, frequency (that is in a range consistent with quasi-static phenomena, such as 0.01 Hz-20 Hz), and wave shape that is output by the transmitter electrode. This changing electric field emitted by the transmitter electrode induces a polarization, or a voltage, on the receiver electrode connected to the QVAR sensor. When both the receiver and transmitter electrode of the device are placed in a patch of soil, the amount of polarization of the receiver electrode changes based on the moisture content of the patch of soil, which enables this new class of soil sensor to detect and monitor the soil moisture level. This may be accomplished in one or more embodiments using the soil sensor depicted in FIG. 1.

FIG. 1 is a component schematic diagram of an electronic device in accordance with some embodiments. In the illustrated embodiment, the electronic device is a soil sensor.

FIG. 1 illustrates a soil sensor 100 capable of measuring the moisture level of a patch of soil 113. Soil sensor 100 comprises a RX-side water-proof casing 101 that protects a power supply 102, a memory 103, a processor 104, a transceiver 105, and an optional filter 107. The components protected by the RX-side water-proof casing 101 are coupled to a charge variation (QVAR) sensor 106.

The components of the RX-side water-proof casing 101 are connected to the components of a TX-side water-proof casing 108, which protects a signal generator 110. The QVAR sensor 106 is coupled to a receiver electrode 112*a*. The receiver electrode 112*a* is enclosed in a case 111*a*, which is composed of dielectric material to protect the receiver electrode from directly contacting the patch of soil 113. The components disposed within the TX-side water-proof casing 108 is connected to a transmitter electrode 112*b*. The transmitter electrode 112*b* is enclosed in a case 111*b*, which is composed of dielectric material to protect the transmitter electrode from directly contacting the patch of soil 113.

The signal generator 110 is a class of electronic devices that can generate electrical signals with set properties of amplitude, frequency, and wave shape. The signal generator 110 may be any suitable device that generates electrical signals with set properties of amplitude, frequency, and wave shape, such as an arbitrary waveform generator (AWG), a pulse generator, or a function generator. After receiving a set of pulse instructions at the transceiver 105, the signal generator 110 generates an electric signal based on those instructions. The set of pulse instructions include an amplitude, a frequency, and a wave shape to be output by the signal generator (e.g., a 5Vpp amplitude, a 10 Hz frequency, and a sine wave shape).

Once the electric signal is generated by the signal generator 110, the electric signal is transmitted through the patch of soil 113 by the transmitter electrode 112*b*. The transmitter electrode 112*b* may be any shape and composed of any material appropriate for transmitting the electric signal generated by the signal generator. In an embodiment, the shape is a cylindrical rod of metal that is enclosed inside of a case 111*b* of suitable dielectric material to protect the transmitter electrode 112*b* from making direct contact with the patch of soil 113. In another embodiment, the shape of the transmitter electrode 112*b* may be a rectangular thin strip of metal on a printed circuit board (PCB). In the case of using the rectangular thin strip of metal as the transmitter electrode, the transmitter electrode is coated (the coating serving the same purpose as the case 111*b*) with a suitable dielectric material to protect the transmitter electrode 112*b* from making direct contact with the patch of soil 113.

After the transmitted signal travels through the patch of soil 113, the transmitted signal is detected at the receiver electrode 112*a* that is located a set distance away from the transmitter electrode 112*b*. The receiver electrode 112*a* is a passive component that has an electric potential induced on it by an external environmental electrostatic field (such as the electrostatic field transmitted through the soil by the transmitter electrode 112*b*). The receiver electrode 112*a* may be any shape and composed of any material appropriate for detecting the electric signal transmitted by the transmitter electrode 112*b*. In an embodiment, the shape is a cylindrical rod of metal that is enclosed inside of a case 111*a* of suitable dielectric material to protect the receiver electrode 112*a* from making direct contact with the patch of soil 113. In another embodiment, the shape of the receiver electrode 112*a* may be a rectangular thin strip of metal on a printed circuit board (PCB). In the case of using the rectangular thin strip of metal as the receiver electrode, the receiver electrode is coated (the coating serving the same purpose as the case 111*a*) in a suitable dielectric material to protect the receiver electrode 112*a* from making direct contact with the patch of soil 113.

The receiver electrode 112*a* receives the transmitted signal, and the received signal is detected by the QVAR sensor 106. The charge variation (QVAR) sensor 106 is coupled to the receiver electrode 112*a*. The QVAR sensor 106 has one differential input (the differential input comprises two input pins), which would allow one receiver electrode to be coupled to the QVAR sensor 106. In this embodiment, the QVAR sensor 106 only has one of the input pins of the differential input connected to a receiver electrode 112*a*. This configuration is advantageous when operating an electrostatic sensor (such as the QVAR sensor 106) for the purpose of soil moisture detection. This configuration results in lower power consumption due to how the electrostatic sensor functions compared to other types of moisture sensors. Electrostatic sensors do not sense by using current flow through the soil, and thus do not consume as much power.

The QVAR sensor functions by detecting a charge differential between the input pins of the differential input. A variation in an external electric field causes a charge polarization of the electrodes that are connected to the input pins of the differential input, which induces an electrical potential on the input pins of the differential input. The induced electrical potential is dependent on the proximity to the source of the electric field and the electrical properties of the material between the source of the varying electric field and the electrodes connected to the differential input. The differential input of the QVAR sensor is compared to a common mode reference, and a difference in electrical potential between the input pins of the differential input will cause a current flow within the circuitry of the QVAR sensor. This current can then be used to detect the presence of materials, and to quantify the amount of material present.

As previously noted in various embodiments, only one of the input pins of the differential input is used and the other input pin of the differential input is left floating at the common mode reference, the common mode signals will not be canceled and the differential potential difference induced on the connected input pin of the differential input will be compared to the common mode reference with no loss of amplitude.

It should be noted that there are distinct differences between soil moisture sensors that use a capacitive sensor in comparison to soil moisture sensors that use an electrostatic sensor, such as the QVAR sensor of this disclosure. The soil moisture sensor based on a QVAR sensor measures the soil moisture content of a patch of soil by quantifying an electric potential difference induced between the two input pins of the QVAR sensor's differential input and correlating the measured potential difference with an amount of polarization of the patch of soil. The polarization of the patch of soil between the electrodes is a result of the polar properties of water (they are polar molecules), the applied electric field polarizes the water molecules causing their dipole to point in the direction of the induced electric field. The QVAR sensor measures the moisture content of the patch of soil by measuring the change in polarization.

A soil moisture sensor that employs a capacitive sensor to measure the soil moisture content of a patch of soil employ frequency measurements to determine a change in capacitance of a capacitor (by measuring the potential difference between the plates of the capacitor). For example, a high frequency voltage signal could be applied across the plates of the capacitor to determine the change in frequency at which the capacitor resonates. Alternately, the change in frequency of a clock coupled to the capacitor placed in the soil can be measured. The frequency changes as a result of the dielectric between the plates of the capacitor changing due to different amounts of water (or moisture) content between the plates. The change in capacitance that results from the change in dielectric can be used to quantify the moisture content of the patch of soil.

Further, a soil moisture sensor that employs a capacitive sensor evaluates the electrical capacitance between two or more electrodes inserted into the soil, while an electrostatic sensor directly deals with charges. In the case of a capacitive sensor, the phenomena that occur are related to the difference in electrical potential between the plates of the capacitor (i.e. the electrodes), $\Delta V = Vplate2 - Vplate1$. In the case of a QVAR sensor, the two electrodes are not referred to each other for a common potential (one electrode generates the potential, while the other one may be connected to the QVAR sensor for sensing). And, when using a QVAR sensor (such as in this disclosure), the dielectric protection used to protect the electrodes from making direct contact with the soil and water prevents any parasitic current between the electrodes (which is not the case for capacitive sensors).

To summarize, the QVAR sensor measures the potential difference between the input pins of the differential input to quantify the soil moisture content of the patch of soil based on the polarization of the water molecules. In comparison, the capacitive sensor measures the change in frequency that results from water content in the soil changing the dielectric between the capacitor plates (which changes the capacitance of the capacitor). Capacitive sensors measure the difference in electrical potential between the plates of the capacitor (between the electrodes). In contrast to capacitive sensors, QVAR sensors implement low frequencies and measure changes in the polarization of the water molecules in the soil (measures the difference in electrical potential between its input pins, not the electrodes). In QVAR sensors, the sensor is in an electrostatic configuration (no current flow), while a capacitive sensor is in an electrodynamic configuration (current flow).

An advantage of using the QVAR sensor 106 for soil moisture sensing in soil sensor 100 is that there is no direct connection made between the transmitter electrode 112*b* and the receiver electrode 112*a* (or the connection has a very large resistance because the connection is the soil between the two dielectric cases 111*a-b*). As a result of the isolation of the two electrodes, there is virtually no current flow between the two electrodes. Thus, because there is virtually no current flow between the electrodes, the power consumption of the soil sensor 100 is minimal, and the soil sensor 100 is more energy efficient than other types of soil sensors.

The QVAR sensor 106 is coupled to the filter 107, which is coupled to the processor 104 of the soil sensor 100. Any sensing information acquired by the QVAR sensor is passed through the filter 107 and then passed to the processor 104 to determine the moisture level of the patch of soil 113. In an embodiment, the sensing information acquired by the QVAR sensor 106 is an alternating signal. This case may use an analog-to-digital converter (ADC) within the QVAR sensor 106 to convert the analog signal into a digital signal to pass through the filter 107 and then to the processor 104.

The detected signal from the QVAR sensor 106 is then passed through the filter 107, which filters out unwanted electrical noise that may be present in the detected signal. The filter 107 may be any suitable type of filter that lets the frequency of the detected signal through to the processor 104 and rejects electrical noise, such as a low-pass filter, or a band-pass filter. Using a low-pass filter, low-frequency signals emanating from the receiver electrode 112*a* and detected by the QVAR sensor 106 may be allowed to pass through while attenuating or reducing the amplitude of higher-frequency signals. In other words, a low-pass filter allows the passage of detected signals from the QVAR sensor 106 having frequencies below a certain cutoff frequency, while blocking or attenuating signals above that frequency. For example, this cut-off frequency could be 50 Hz to avoid signals from electricity grids nearby, which typically run at 60 Hz. In another embodiment, a band-pass filter may be used to allow detected signals by the QVAR sensor 106 having a specific range of frequencies, known as the passband, to pass through while attenuating or blocking frequencies outside that range. In other words, a band-pass filter selectively allows signals within a certain frequency range to pass through while rejecting or attenuating signals both below and above that range. In another embodiment, the filter 107 may be an algorithm implemented in software. After the detected signal by the QVAR sensor 106 has been filtered by the filter 107, the filtered signal is passed to the processor 104 to extract the soil moisture content of the patch of soil 113.

In certain embodiments, the processor 104 of the soil sensor 100 executes instructions that are stored in the memory 103 of the device. The instructions tell the processor 104 how to process signals detected by the QVAR sensor 106. The processor processes the signal to extract the soil moisture content of the patch of soil 113, and the soil moisture content information can then be stored in the memory 103 with a timestamp. In other embodiments, the soil moisture content may be actively transmitted to an external receiver using the transceiver 105 for real-time display and monitoring of the moisture content of the soil. The processor 104 may be any component or collection of components adapted to perform computations or other processing-related tasks related to the methods disclosed herein. Processor 104 can be, for example, a microprocessor, a microcontroller, a control circuit, a digital signal processor, a field-programmable gate array (FPGA), an application-specific integrated circuit (ASIC), a system-on-chip (SoC), or combinations thereof.

Memory 103 may be any component or collection of components adapted to store programming, event information, or instructions for execution by the processor 104. In an embodiment, memory 103 includes a non-transitory computer-readable medium. The non-transitory computer-readable medium includes all types of computer-readable media, including magnetic storage media, optical storage media, flash media, and solid-state storage media.

It should be understood that software can be installed in and sold with soil sensor 100. Alternatively, the software can be obtained and loaded into soil sensor 100, including obtaining the software through a physical medium or distribution system, including, for example, from a server owned by the software creator or from a server not owned but used by the software creator. The software can be stored on a server for distribution over the Internet, for example.

In various embodiments, memory 103 is a dedicated non-transitory memory storage for storing instructions or data specific to determining soil moisture levels. In other embodiments, memory 103 may refer to existing memory storage to store soil moisture level measurements made by the soil sensor. In other embodiments, memory 103 may have the functionality of both of the previous embodiments. The memory 103 may include non-volatile memory, read only memory, or random access memory.

The transceiver 105 may be any device suitable for acting as both a transmitter and a receiver for the soil sensor 100 such as a RF transceiver or a radio transceiver. The transceiver 105 may be integrated with the QVAR sensor 106 or separate from it in various embodiments. A transceiver is a device that combines both transmitter and receiver functions, allowing for two-way communication. The transceiver 105 acts as a receiver to receive configuration instructions for the signal generator, to receive instructions to send soil moisture information stored in memory 103, and to receive a start or end data taking instruction for the soil sensor 100. The transceiver 105 acts as a transmitter to transmit status of the soil sensor (such as the sensor is operational, or actively taking data), and to transmit the soil moisture information when queried to do so, or in real time (depending on the configuration the soil sensor has received instructions to operate in). In some embodiments, the receiver and transmitter functionalities of the transceiver 105 may also be implemented independently.

The power supply 102 provides power for the operation of all of the electronic components that are enclosed in RX-side water-proof case 101. The power supply 102 may be any suitable electronic device, such as a battery power supply, a linear power supply, a switched-mode power supply (SMPS), an uninterruptible power supply, a solar power supply, or combinations thereof.

The RX-side and TX-side water-proof cases 101 and 108 protect their corresponding electronic components from water in the soil sensor operating environment. The cases may be made from any suitable material that will keep water from penetrating to the electronic components. In various embodiments, the RX-side and TX-side water-proof cases 101 and 108 may include polycarbonate, thermoplastic elastomer (TPE), thermoplastic polyurethane (TPU), silicone, or other water-proof plastics. In addition, the RX-side and TX-side water-proof cases 101 and 108 may be sealed with washers, o-rings, and others to ensure and prevent water penetration through joints. In certain embodiments, the RX-side and TX-side water-proof cases 101 and 108 may be sealed to industry standards such as IP55, IP 56, and IP65. In various embodiments, the RX-side and TX-side water-proof cases 101 and 108 may be sealed against dust and moisture penetration. In various embodiments, the RX-side and TX-side water-proof cases 101 and 108 may be sealed to have an IP rating of IPxy, where x is greater than 3 and y is greater than 2. In various embodiments, the RX-side and TX-side water-proof cases 101 and 108 may hermetically seal the components within.

In another embodiment, rather than having two water-proof cases, a single water proof case that protects all of the electronic devices of the soil sensor may be used. Such an integrated case may be formed to have similar properties discussed above.

In various embodiments, an electrode of the soil sensor includes at least two layers. The first layer provides an external interface to the environment surrounding the soil sensor 100, which in response to an external electrostatic field becomes polarized. The first layer includes a dielectric material (or dielectric case 111*a-b*), characterized as a good insulator with good relative electric permittivity. For example, the first layer may be polytetrafluoroethylene, polyimide, glass, polyester, metal oxides, or the like. The second layer includes a conductive material, which senses the potential of the first layer, and forms the main electrode (such as the receiver electrode 112*a* or the transmitter electrode 112*b*). For example, the second layer may be metal (e.g., copper), a metal alloy, or the like.

The potential induced at receiver electrode 112*a* varies depending on, for example, the size, geometry, and placement of electrodes 112*a-b* with respect to each other and soil sensor 100.

Receiver electrode 112*a*, and any other input pin of the differential input of the QVAR sensor 106 have a common reference, and the changing electric field emitted by the transmitter electrode 112*b* through the patch of soil 113 induces an electric potential at the receiver electrode 112*a*. Because receiver electrode 112*a* and the other input pin of the differential input of the QVAR sensor 106 have a common reference, the difference in distance between the receiver electrode 112*a* and the transmitter electrode 112*b* provides a detectable differential potential between the receiver electrode 112*a* and the other input pin of the differential input of the QVAR sensor 106 that is left floating at each moment in time.

Figure 2:
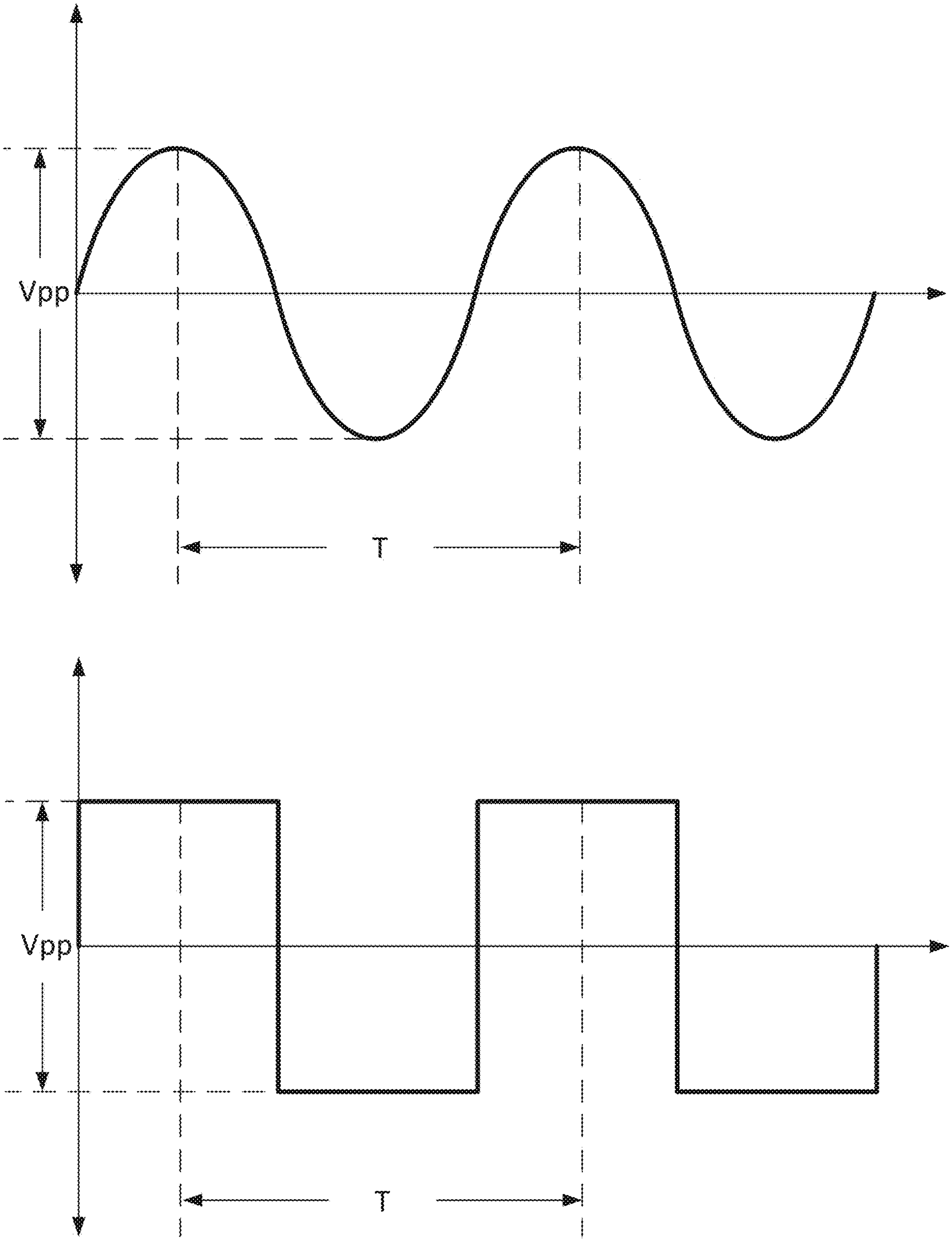
FIG. 2 illustrates two plots that depict two types of waveforms that can be output by a signal generator.

FIG. 2 illustrates two different types of signals that a signal generator is capable of outputting. As mentioned above, the signal generator outputs electrical signals that are characterized by an amplitude, a frequency, and a wave shape. Both plots show a waveform that has a peak-to-peak voltage Vpp, and an oscillation period T. The vertical axis of the plots is voltage, and the horizontal axis of the plots is time. The peak-to-peak voltage is correlated to the amplitude of the waveform. The oscillation period is inversely proportional to the frequency of the waveform.

In an embodiment, the signal generator may receive instructions to output a waveform like the one depicted in the top plot of FIG. 2, which is a sine wave. For example, the waveform could be a 5Vpp amplitude, a 10 Hz frequency (which is a 0.1 s oscillation period), and a wave shape of a sine wave.

In another embodiment, the signal generator may receive instructions to output a waveform like the one depicted in the bottom plot of FIG. 2, which is a square wave. For example, the waveform could be a 5Vpp amplitude, a 10 Hz frequency (which is a 0.1 s oscillation period), and a wave shape of a square wave.

Though they are not explicitly shown in FIG. 2, signal generators can output more wave types than a sine wave, or a square wave. For example, the signal generator may output triangular waves, pulse waves, cardiac pattern waves, gaussian pulse waves, and arbitrary waves, as well as sine waves and square waves. In certain embodiments, the waves may comprise pulse trains with only positive pulses.

In various embodiments, the frequency is selected to minimize interference from other noise sources in the area. For example, if the soil sensor is placed near electrical utilities or electrical cables carrying power, the frequency is designed to be below 60 Hz. Similarly, if the location is near other equipment causing electromagnetic pulse noise, the frequency may be modified to minimize interference.

Figure 3:
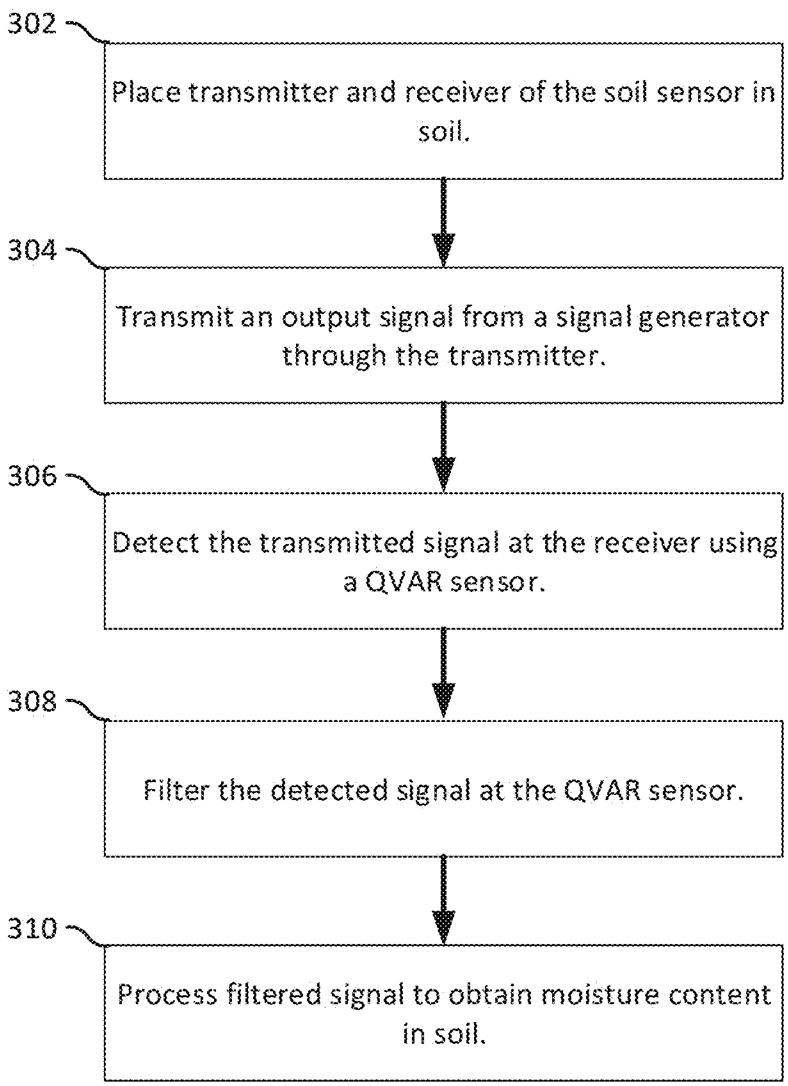
FIG. 3 is a flowchart of a soil moisture detection method capable of determining the moisture level of a patch of soil.
Figure 5A:
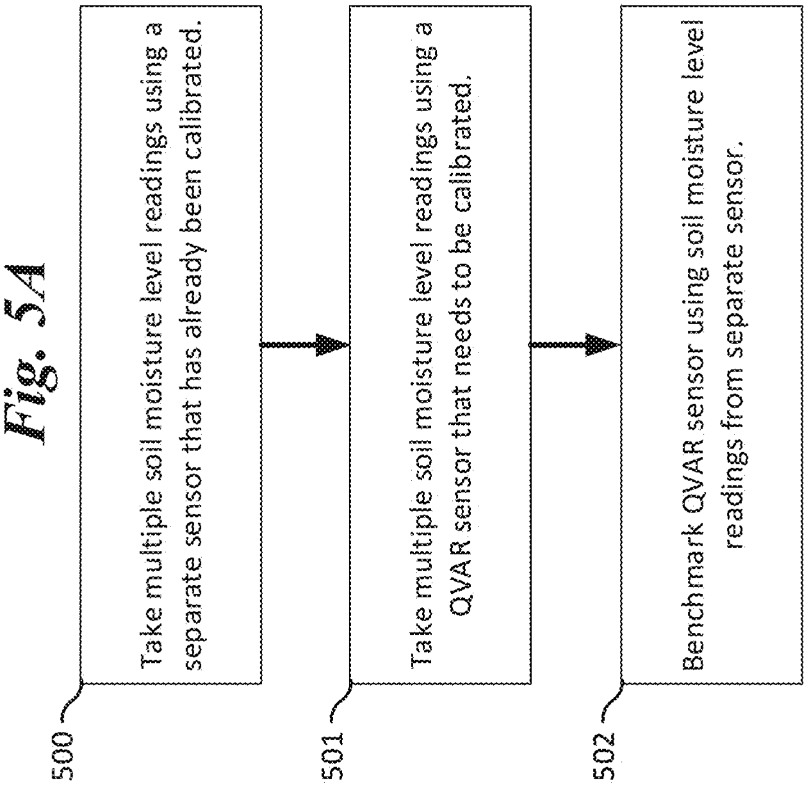
FIGS. 5A-5B are flowcharts of two different methods of calibrating a soil moisture sensor in accordance with some embodiments.
Figure 5B:
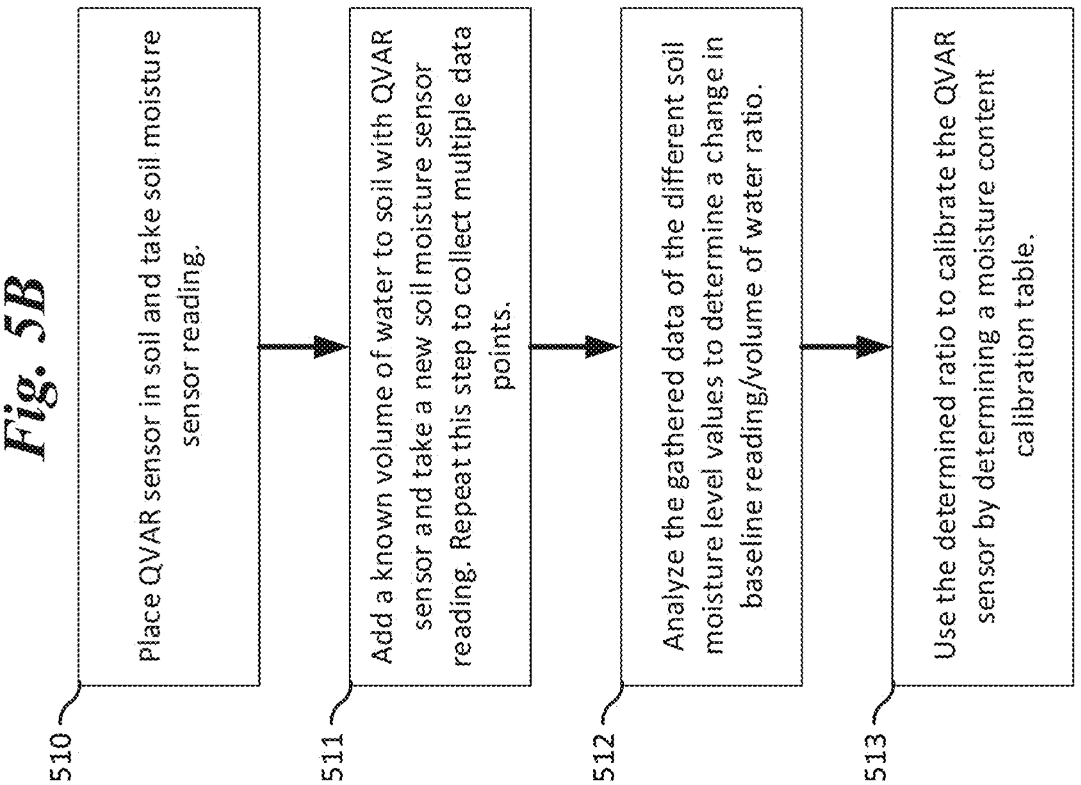

The flowchart of FIG. 3 illustrates a method for operating the soil sensor 100 to determine the soil moisture level of a patch of soil. This embodiment method assumes that the soil sensor 100 has already been calibrated for the particular soil. Methods for the calibration of the soil sensor 100 are shown in FIGS. 5A and 5B, and are discussed later on in this document.

The method begins at box 302 with the initial placement of the soil sensor 100. The transmitter electrode (isolated in its dielectric case) and the receiver electrode (isolated in its dielectric case) of the soil sensor 100 may be placed in a patch of soil. Because the two electrodes are in their respective dielectric cases, they do not make direct contact with the soil. The separation distance between the receiver and transmitter electrodes is in the range of 1-5 cm.

Once the receiver and transmitter electrodes have been placed in the soil, the method moves to box 304. In box 304, an output signal is generated and output by the signal generator through the transmitter electrode into the soil. The output signal is a time-varying electric potential induced on the transmitter electrode by the signal generator. The time-varying electric potential causes a time-varying electric field to be induced through the soil. The soil and any water between the receiver and transmitter electrode are polarized by the time-varying electric field.

After the output signal has been generated and output by the transmitter electrode into the soil, the method moves to box 306. The polarization of the material between the transmitter and receiver electrode is detectable by the receiver electrode. In box 306, the polarization of the material between the receiver and transmitter electrode induces an electric potential on the receiver electrode. In other words, the receiver electrode is connected to a QVAR sensor, which detects the transmitted signal on the receiver electrode. The electric potential induced on the receiver electrode is sensed by the QVAR sensor 106. As mentioned in the detailed description of FIG. 1, this results in a difference in potential between the input pins of the differential input of the QVAR sensor that the receiver electrode is connected to and the common mode reference of the QVAR sensor. That difference in potential causes an electrical current to flow in the device, and this information may be processed to extract the soil moisture content.

The detected signal at the receiver electrode by the QVAR sensor may be filtered to remove any erroneous noise from the environment (box 308). The method, after moving to box 308, filters out any noise in the detected signal by using a filter. The filter can be any type of filter that does not remove the detected signal, such as a low-pass filter, a band-pass filter, a high-pass filter, as well as other filters that may have multiple band-passes. In an embodiment, the transmitted signal is of a frequency of 10 Hz. Thus, the filter may allow a 10 Hz signal to pass through to the processor.

In box 310, the digital signal output from the QVAR sensor is processed by the processor 104 using instructions from the memory 103 to extract the moisture level of the material between the receiver electrode and the transmitter electrode. This may be performed by applying a benchmark function or looking up a calibration table and comparing the value of the digital signal from the QVAR sensor to values in the calibration table. The calibration table is described in further embodiments described using FIGS. 4, 5A and 5B. After the moisture level is attained, the information can be stored in the soil sensor, or transmitted to a device for further analysis, or a combination of both of these.

The method shown in the flowchart of FIG. 3 can be operated in different ways. In an embodiment, the method may be a continuous reading process, where the moisture level is constantly being monitored. In other embodiments, the method may be instructed to take readings over a configurable timeframe. In other embodiments, the method is used to provide readings when the soil sensor 100 has been connected to an irrigation control system. An example output of the soil sensor 100 will now be discussed.

Figure 4:
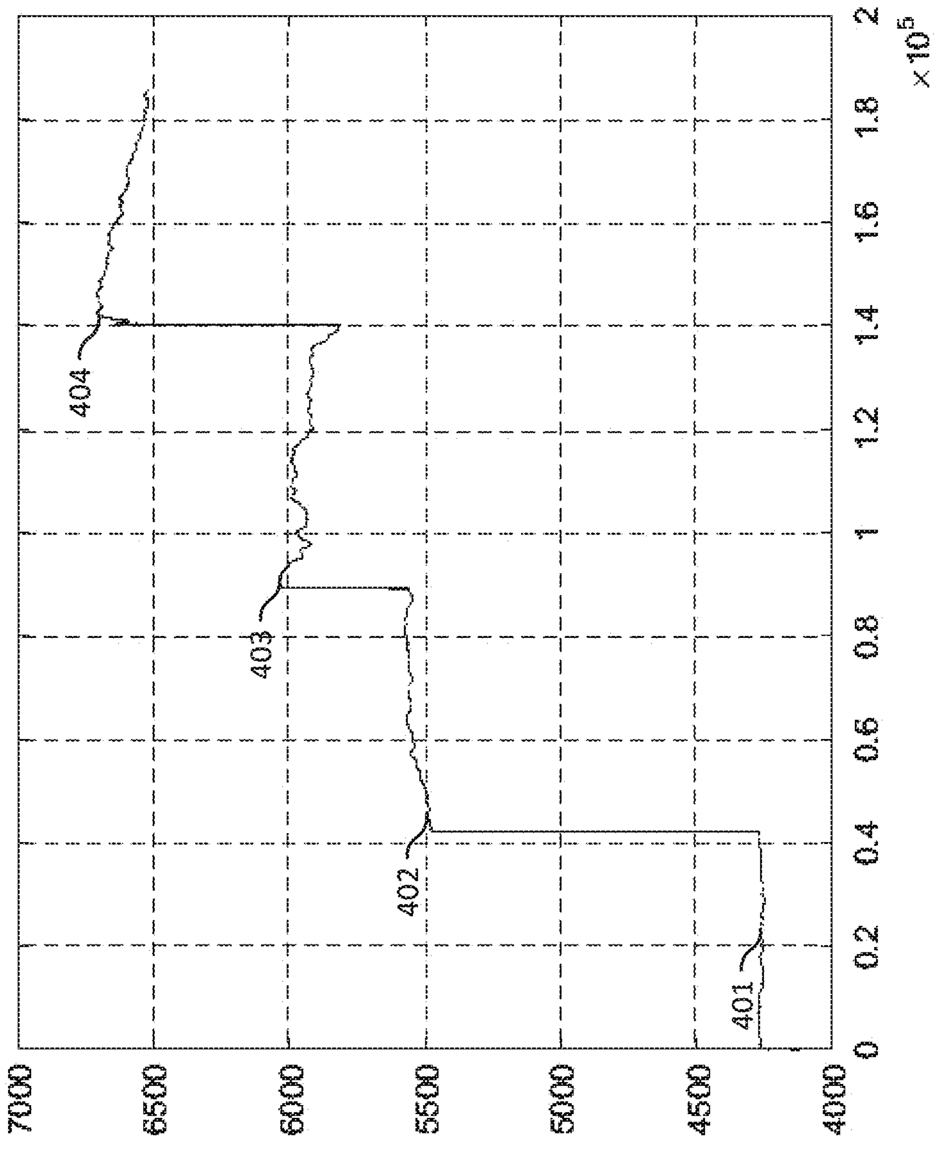
FIG. 4 is a plot illustrating the output of a soil moisture sensor that has been placed in a patch of soil and had different amounts of water added.

FIG. 4 is a plot schematically illustrating the output of the soil sensor 100 which is the moisture level over a timeframe. The vertical axis corresponds to the moisture level of the patch of soil, and the horizontal axis corresponds to time. The plot shows the soil sensor output in an embodiment where the soil sensor started in a dry patch of soil, and a known volume of water was added to the soil at three specific times. The volume of water that was added to the soil was the same at all three times (e.g., a cup of water was added to the soil every 45 seconds).

A baseline moisture level of the patch of soil is shown at the start of the plot of FIG. 4. This baseline 401 is an initial measurement of the soil moisture level of the patch of soil before the addition of a known volume of water (e.g., a single cup) to the patch of soil. After taking this baseline 401 measurement, a single cup of water is added to the patch of soil. The addition of the water causes the reading of the soil sensor 100 to sharply rise in level to the new moisture level 402 of the soil.

After the addition of the single cup of water to the patch of soil, there is a pause for a relatively short timeframe (approximately 45 seconds) to let the water added to the patch of soil saturate it, and give a stable reading at the new moisture level 402 of the patch of soil. After the short timeframe had passed, a second cup of water is added to the patch of soil, which corresponds to a new sharp rise in moisture level to a new soil moisture level 403 of the patch of soil.

Once the second cup of water is added to the patch of soil, there is a pause of the same timeframe (approximately 45 seconds) to let the water added to the patch of soil saturate it, and give a stable reading at the new soil moisture level 403. It is evident from the plot of FIG. 4, that at the new soil moisture level 403, the patch of soil is not reaching as stable of a moisture level reading as the previous measurement levels. This is a result of the large amount of water now present in the patch of soil. The quantity of water present will take longer to move around and find regions of the patch of soil that are not completely saturated yet. The water moves out of the region where it was added (which is between the two electrodes of the soil sensor) into regions of the patch of soil that are not saturated yet. This behavior is evidenced by the slow decline in moisture level that is depicted in the soil moisture level 403.

Again, after waiting the same timeframe (approximately 45 seconds), another single cup of water (bringing the total to three cups of water) is added to the patch of soil. This final addition of water raised the soil moisture level 403 to a new soil moisture level 404. As a result of the increasing saturation levels of the patch of soil, the water will move around to find regions of the soil that are not fully saturated. This movement of water from the region between the two electrodes of the soil sensor causes the slow decline in moisture level that is observed in the plot of FIG. 4 at the soil moisture level 404. FIG. 4 shows the moisture level determining capabilities of the soil sensor of this disclosure.

In order to detect the moisture level of a patch of soil with the highest accuracy, the soil sensor of this disclosure may be calibrated to the environment that it will operate in. Two different methods of calibrating the soil sensor are depicted in the flowcharts of FIGS. 5A and 5B.

The flowchart illustrated in FIG. 5A depicts a calibration method for a soil sensor that uses a separate (already calibrated) soil sensor as the calibration reference to benchmark the soil sensor of this disclosure. The separate soil sensor calibration method of FIG. 5A begins in box 500. At box 500, a reference soil sensor that has already been calibrated is placed in a patch of soil. It should be understood that the reference soil sensor does not necessarily have to be the same type of soil sensor described in this disclosure. The reference soil sensor could be any type of soil sensor with a comparable soil moisture level reading as the soil sensor of this disclosure. Once the reference soil sensor is placed in the patch of soil, multiple soil moisture level readings are determined, for example, at different water content or even without changing moisture content of the soil.

After recording the multiple soil moisture level readings made using the already calibrated soil sensor, the separate soil sensor calibration method then proceeds to box 501. In box 501, a soil sensor of the same type as this disclosure, that needs to be calibrated, is placed in the same patch of soil that the already calibrated soil sensor was previously located in. Once the soil sensor that needs to be calibrated is located in the same patch of soil, multiple soil moisture level readings are determined for the same conditions as the reference soil sensor.

Referring next to box 502, the soil sensor of the same type of this disclosure's soil moisture level readings are compared to the soil moisture level readings from the reference soil sensor. Because the moisture level readings of the reference soil sensor correspond to a known moisture level, the soil moisture level readings of the soil sensor of the same type as this disclosure can be benchmarked to the same soil moisture level value. Once this benchmark is made between the two soil sensors, the soil sensor of the same type as this disclosure is calibrated. The difference between the sensors may be stored as a benchmark function which could easily be applied to the output from the soil sensor being calibrated or a look up calibration table in one or more embodiments.

FIG. 5B shows an illustration of a flowchart of a soil sensor calibration method that only requires the soil sensor that needs to be calibrated, rather than two soil sensors (one already calibrated, and the other needing to be calibrated). The main advantage of the calibration method of FIG. 5B over the one illustrated in FIG. 5A is that the calibration method of FIG. 5B only uses a single soil sensor. The calibration method of FIG. 5B does require more steps than the calibration method of FIG. 5A. The calibration method of FIG. 5B uses a moisture content calibration table to calibrate the soil sensor.

The calibration method of FIG. 5B begins in box 510. In box 510, the soil sensor that needs to be calibrated is placed in a patch of soil and a soil moisture level reading is recorded. Once the soil moisture level reading is recorded, the calibration method proceeds to box 511.

Once the calibration method of FIG. 5B is in box 511, a known volume of water is added to the patch of soil. The soil sensor is then used to record a new soil moisture level reading that corresponds to the new soil moisture level. The process of box 511 is repeated multiple times with the addition of a known volume of water each time. This repetition is done to collect multiple data points at known volumes of water levels for the patch of soil.

After taking multiple moisture level readings like discussed above as a part of box 511, the calibration method moves to box 512. In box 512, the data that was gathered in boxes 510-511 is analyzed to determine a change in soil moisture level/known volume of water ratio. The ratio can then be used to form a moisture content calibration table.

After determining the ratio of box 512, the calibration method of FIG. 5B proceeds to box 513. In box 513, the ratio determined in box 512 is used to construct a moisture content calibration table. The moisture content calibration table is then used as a calibration tool to convert readings of the soil sensor into actual soil moisture level values. Once the moisture content calibration table has been constructed, the soil sensor has been calibrated and can be used to make accurate soil moisture level readings.

Figure 6:
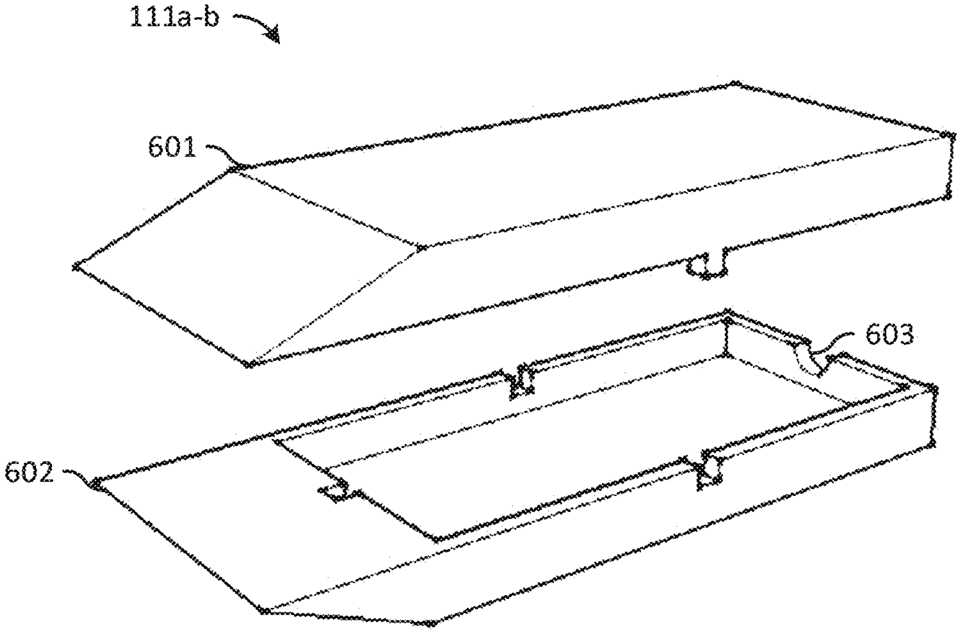
FIG. 6 is a diagram of a dielectric casing used to cover the electrodes of the soil moisture sensor in an embodiment.

FIG. 6 illustrates a dielectric case that may be used to isolate the transmitter electrode 112*b* or receiver electrode 112*a* from the patch of soil 113 they occupy, in an embodiment. The dielectric case illustrated in FIG. 6 can be used as the dielectric cases illustrated and labeled as 111*a* and 111*b* in FIG. 1. As mentioned before, the dielectric case may be composed of any material that provides sufficient protection from the patch of soil the soil sensor is placed in, such as polytetrafluoroethylene, polyimide, glass, polyester, metal oxides, or the like.

In FIG. 6, in an embodiment, the top of the dielectric case 601, and the bottom of the dielectric case 602 are both composed of the same material, and are assembled with the electrode placed inside of the hole 603. In another embodiment, the top of the dielectric case 601 and the bottom of the dielectric case 602 may be composed of different materials.

The top of the dielectric case 601 and the bottom of the dielectric case 602 may be assembled around the electrode by gluing, or epoxying the two halves together in order to form a water-proof seal. Once assembled together, the hole 603 is sealed around the connection from the electrode (that is inside of the dielectric case) to the proper circuit that corresponds to each electrode. This is done to prevent any water from going inside of the dielectric case and contacting an electrode. The dielectric case may be constructed using typical machining processes, molds, or even 3D printing techniques.

An advantage of using dielectric material that is waterproof to cover the electrodes is that the metal electrodes do not make direct contact with the patch of soil that the soil sensor is placed in. As a result, the electrodes are protected from corrosion causing elements that are present in the patch of soil. Thus, the electrodes of the soil sensor 100 of this disclosure will not corrode over time, unlike many of the other types of soil sensor currently on the market.

Figure 7:
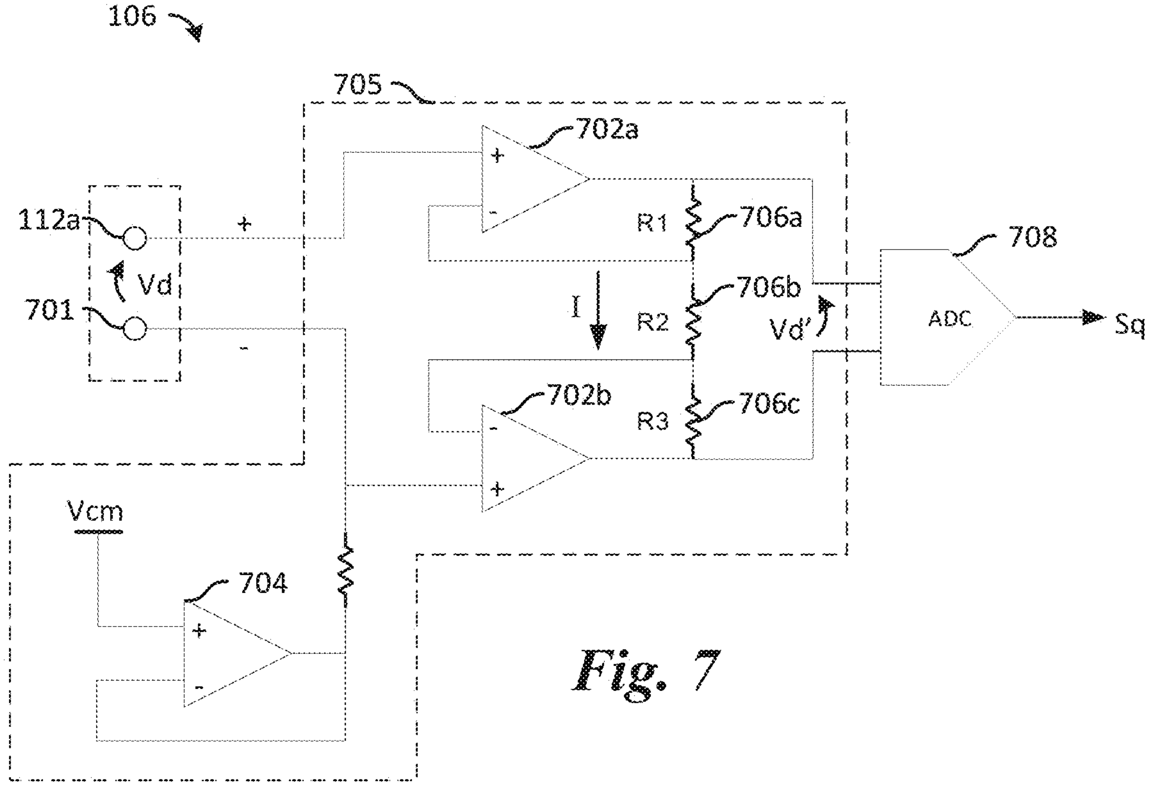
FIG. 7 is a schematic diagram of an analog-front-end circuit (AFE) and an analog-to-digital converter (ADC) of a charge variation (QVAR) sensor in an embodiment.

FIG. 7 illustrates an analog front end (AFE) circuit 705 and an ADC 708 of a QVAR sensor 106, which may be installed in soil sensor 100. As shown, AFE 705 includes operational amplifiers 702*a*-*b*, biasing stage 704, R1, R2, and R3 resistors 706*a*-*c*, and the analog-to-digital converter (ADC) 708. The pair of input electrodes—receiver electrode 112*a* and floating input 701 represent the input pins of the differential input to QVAR sensor 106 and are coupled to the AFE 705, where, in this embodiment, floating input 701 is left floating. The potential difference between the receiver electrode 112*a* and the floating input 701 is illustrated as voltage Vd. The biasing stage 704 (i.e., buffer stage) biases AFE 705 at a common-mode voltage Vcm.

The inverting terminals of operational amplifiers 702*a*-*b* are connected by R2 resistor 706*b*. The potential difference between the receiver electrode 112*a* and the floating input 701 generates a current through R2 resistor 706*b* of I=Vd/R2. This current traverses through R1, R2, and R3 resistors 706*a*-*c*, and assuming R1=R3, an output voltage Vd' is produced at the input of the ADC 708 given by Vd'=I(2R1+R2) or equivalently Vd(2(R1/R2)+1).

The differential potential Vd', which is proportional to the differential potential Vd is supplied to the input of ADC 708. ADC 708 converts the analog voltage to a digital charge-variation signal Sq, which is subsequently transferred to processor 104. It is understood that the total gain of QVAR sensor 106 depends primarily on R2 resistor 706*b* and can be, thus, adjusted by the appropriate selection of the value of R2 resistor 706*b*.

In an embodiment, the charge-variation signal Sq is a high-resolution (16-bit or 24-bit) digital stream. ADC 708 is optional in so far as processor 104 can be configured to work directly on the analog signal or can itself comprise an analog-to-digital converter adapted to convert the signal Vd'.

Figure 8:
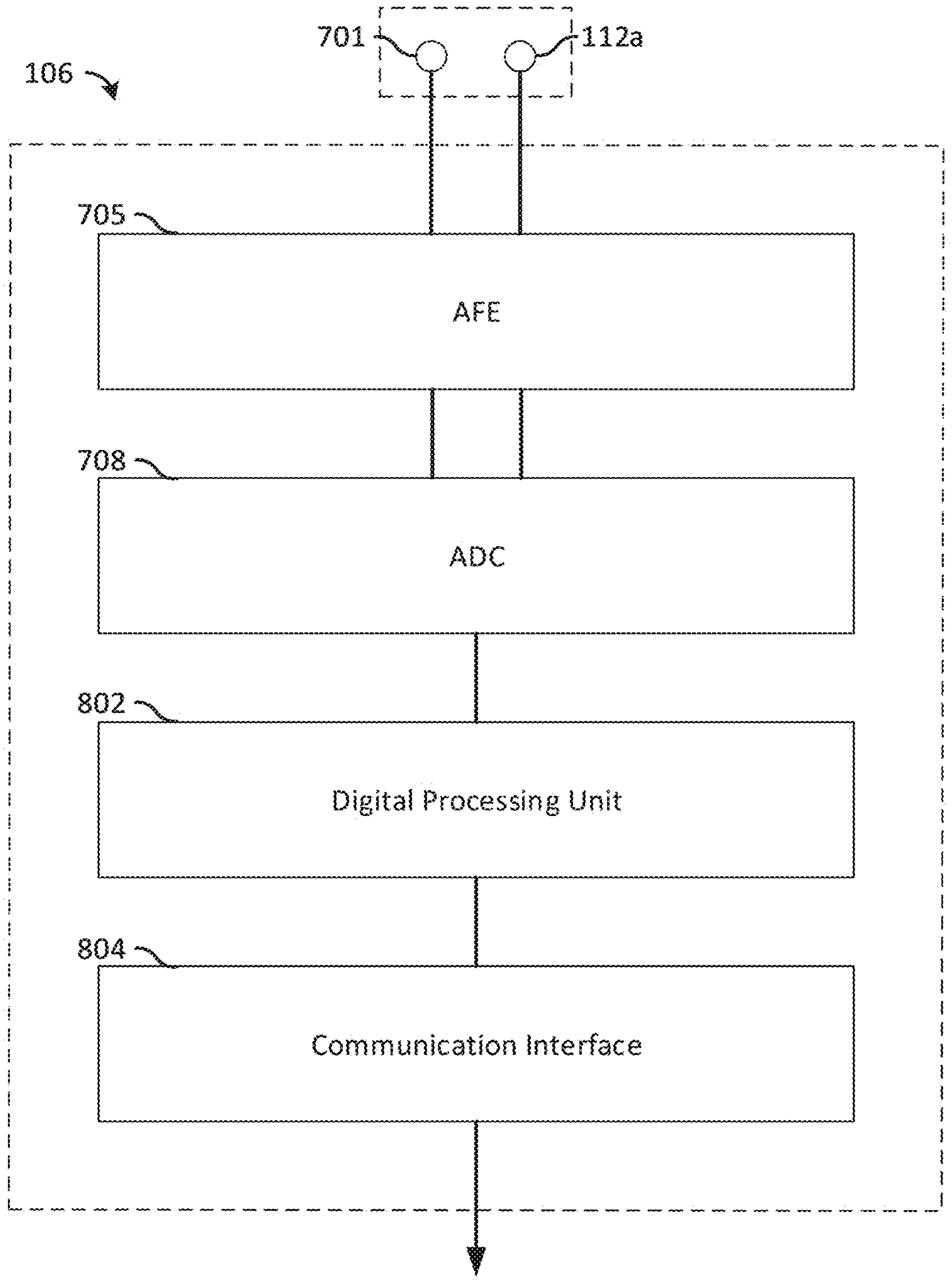
FIG. 8 is a schematic diagram of the elements of a QVAR sensor in an embodiment.

FIG. 8 is a schematic diagram of the QVAR sensor 106, in an embodiment. The QVAR sensor 106 comprises the analog-front-end circuit (AFE) 705, the analog-to-digital converter (ADC) 708, a digital processing unit 802, and a communication interface 804, in an embodiment. The receiver electrode 112*a* and floating input 701 are coupled to the input pins of the differential input and are coupled to the AFE 705, which is illustrated in FIG. 7. The AFE 705 is illustrated in FIG. 7 and detailed in the description above. The AFE 705 sends the detected analog signal (such as Vd' in FIG. 7) to the ADC 708.

The ADC 708 converts a detected analog signal from the AFE 705 into a digital charge variation signal (such as Sq in FIG. 7) for processing by the digital processing unit 802. In an embodiment, there is no ADC 708 inside the QVAR sensor 106 and instead there is an ADC in the soil sensor 100.

The digital processing unit 802 may be any processor that processes the digital charge variation signal from the ADC 708 to quantify a QVAR signal detected by the QVAR sensor 106. After processing the digital charge variation signal from the ADC 708, the digital processing unit 802 communicates the processed charge variation signal by sending the processed charge variation signal through the communication interface 804.

The communication interface 804 may be any communication interface that enables the transfer of the processed charge variation signal from the QVAR sensor 106 to other elements that comprise the soil sensor 100. For example, the communication interface may be an I2C or an SPI format.

Figure 9A:
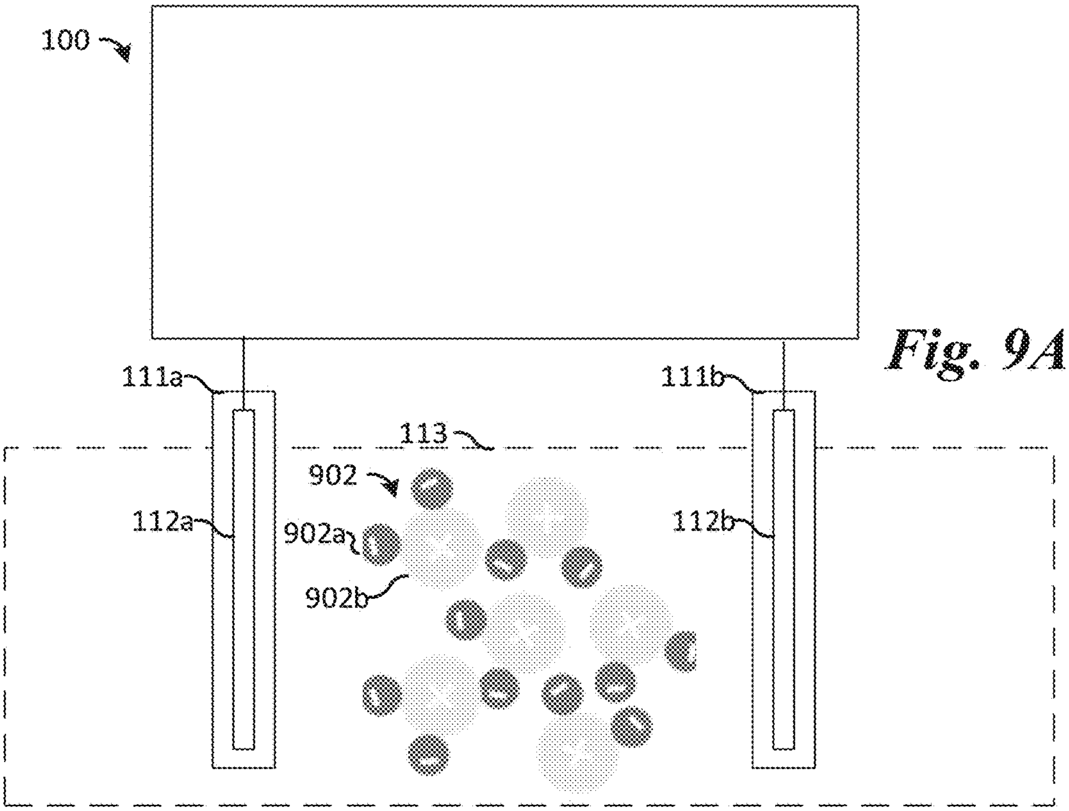
FIGS. 9A-9B are diagrams that illustrate the polarization of water molecules between the electrodes of the soil sensor in an embodiment.
Figure 9B:
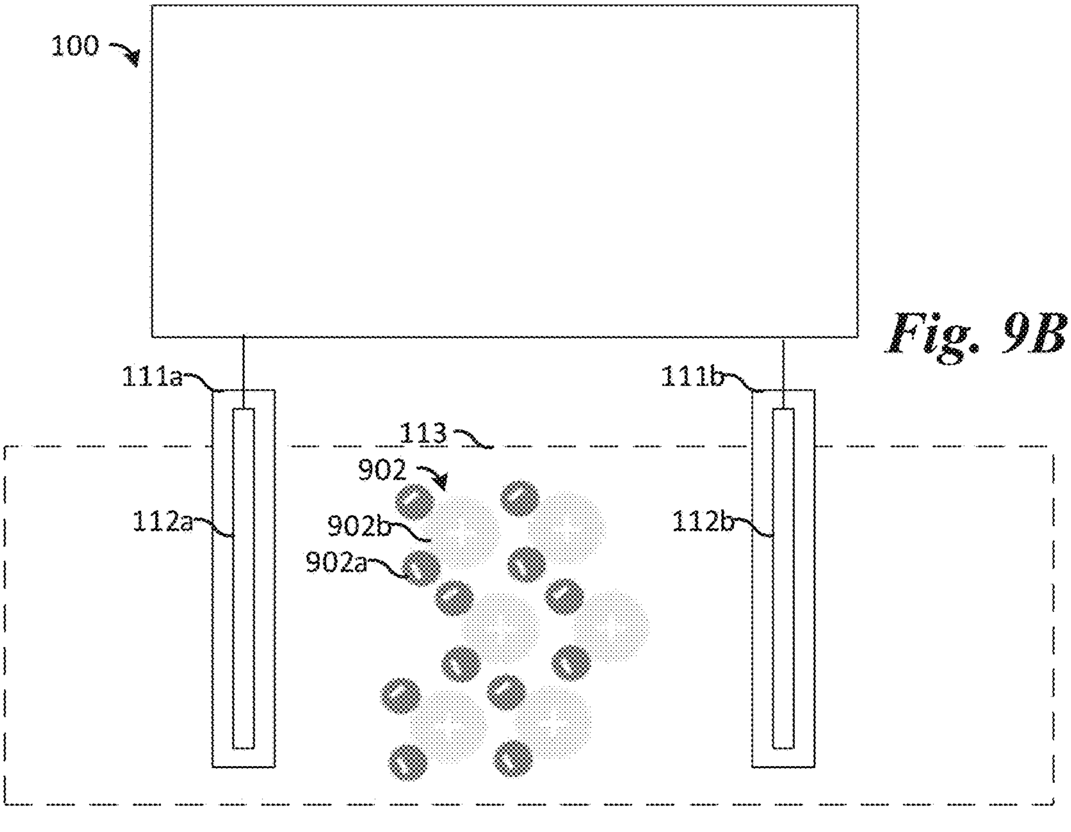

FIGS. 9A-9B are diagrams to illustrate the polarization of the water molecules 902 that are in the patch of soil 113 caused by the operation of the soil sensor 100 of this disclosure. The soil sensor 100 illustrates the receiver electrode 112*a* in the receiver dielectric case 111*a* and the transmitter electrode 112*b* in the transmitter dielectric case 111*b* placed a fixed distance apart in a patch of soil 113. Between the two electrodes is the patch of soil 113 which has water molecules 902 present in the soil. The water molecules 902 (H═O═H) are polar molecules, and are illustrated with their two hydrogen atoms 902*a* bonded with their single oxygen atom 902*b*. As a result of the distribution of the hydrogen atoms 902*a* around the more electrically positive nucleus of the oxygen atom 902*b* (which causes one end of the molecule to be more positive and the other end to be more negative), an electric dipole is naturally formed. Molecules that have one end more positive and the other end more negative form dipoles and are called polar molecules. When exposed to an external electric field, polar molecules align with their dipoles pointed in the direction of the electric field.

FIG. 9A is an illustration of the random configuration of the water molecules 902 when no signal is output through the transmitting electrode 112*b* by the signal generator. The water molecules 902 are randomly oriented and their dipoles do not align to any external electric field. When the water molecules 902 are randomly oriented like shown in FIG. 9A, the water molecules 902 are not polarized. When the signal generator is not outputting a signal, the water molecules 902 will remain in the random orientation and the patch of soil 113 (which includes the soil and the water molecules 902) is in electrostatic equilibrium (i.e., they are at the same potential).

FIG. 9B illustrates the configuration of the water molecules 902 after the signal generator has been activated. The water molecules 902 have aligned with the electric field that is output from the signal generator. The dipoles of the water molecules 902 align in the direction of the electric field. As a result, the water molecules are aligned, called polarized. The polarized water molecules 902 have the hydrogen atoms 902*a* on the side of the transmitter electrode 112*b* and the oxygen atoms 902*b* on the side of the receiver electrode 112*a*. Though the water molecules 902 are polarized, there is no charge movement between the electrodes of the soil sensor 100. Thus, the soil sensor 100 is operating electrostatically (no current flow between the electrodes).

Once the QVAR of the soil sensor 100 is turned on, the QVAR will measure the variation of charges present in the patch of soil 113 under the polarization effect. In other words, the QVAR detects a potential difference between the input pins of its differential input that results from the polarization of the water molecules 902 present in the patch of soil 113 inducing a signal on the receiver electrode 112*a*. The induced signal on the receiver electrode 112*a* is different from the output signal from the transmitter electrode 112*b* because of the polarization of the water molecules 902 in the patch of soil 113.

Figure 10A:
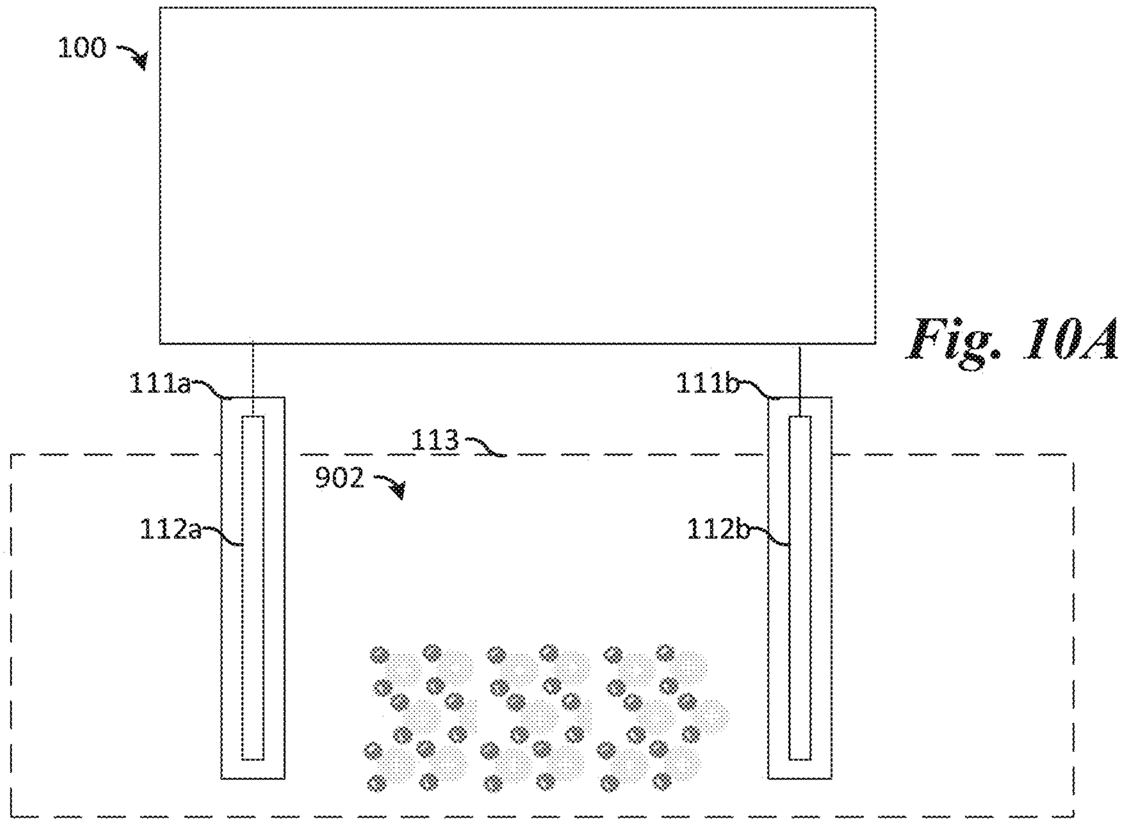
FIGS. 10A-10B are diagrams that illustrate the polarization of water molecules between the electrodes of the soil sensor at different quantities of water in the soil.
Figure 10B:
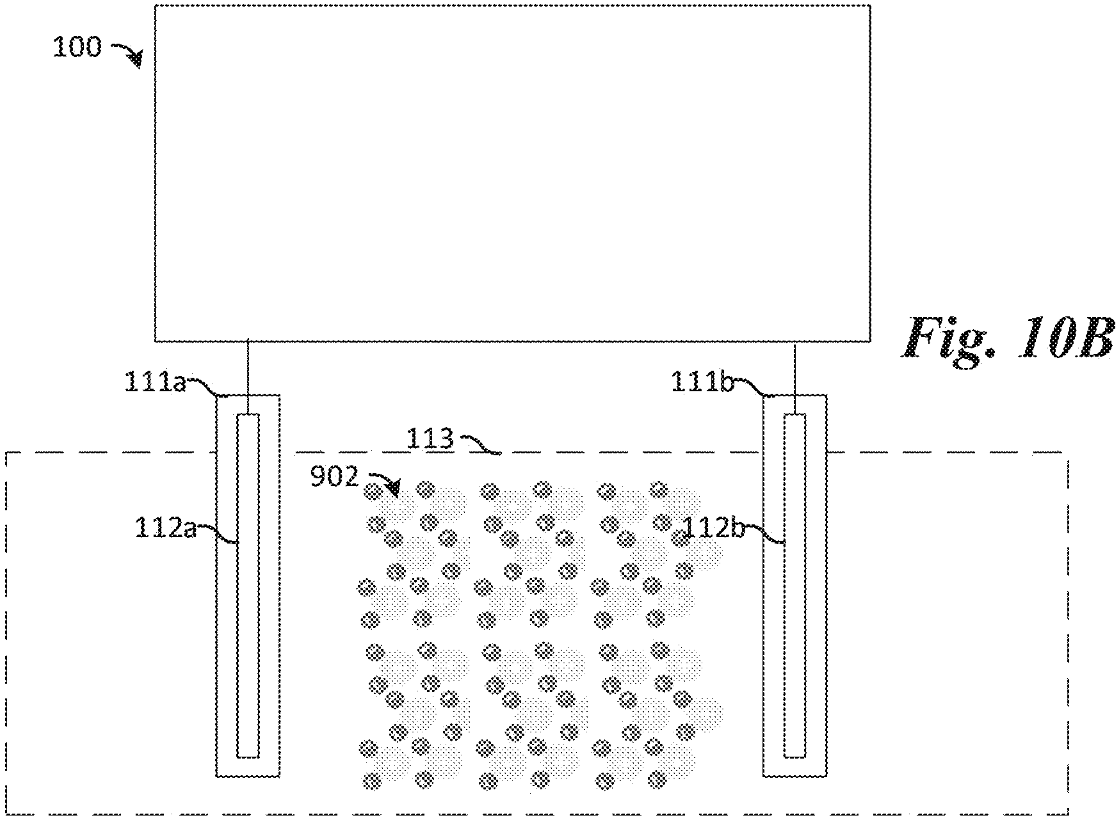

FIGS. 10A-B illustrate the configuration of the water molecules 902 with different amounts of water present in the patch of soil 113. The figures show varying amounts of water in the patch of soil 113. The polarization of the water molecules 902 is a result of the operation of the soil sensor 100, which has the receiver electrode 112*a* in the receiver dielectric case 111*a* positioned a fixed distance from the transmitter electrode 112*b* in the transmitter dielectric case 111*b*. FIGS. 10A-B illustrate different quantities of polarized water molecules 902 in the patch of soil 113. FIG. 10A shows a small amount of water molecules 902, and FIG. 10B shows a large amount of water molecules 902. The water molecules 902 in FIGS. 10A-B are all polarized.

FIG. 10A illustration a level of moisture content that may be an initial measurement level. In an embodiment, as an example, FIG. 10A illustrates a quantity of water molecules 902 in the patch of soil 113 that may be consistent with the level of moisture content illustrated at the baseline 401 soil moisture level in FIG. 4. Measurements made by the soil sensor 100 may output soil moisture levels consistent with the baseline 401 soil moisture level illustrated in FIG. 4.

FIG. 10B illustration a level of moisture content that is a full saturation level of the patch of soil 113. In an embodiment, as another example, FIG. 10B illustrates a quantity of water molecules 902 in the patch of soil 113 that may be consistent with the level of moisture content illustrated at the soil moisture level 404 in FIG. 4. Measurements made by the soil sensor 100 may output soil moisture levels consistent with the soil moisture level 404 illustrated in FIG. 4.

Example embodiments of the invention are described below. Other embodiments can also be understood from the entirety of the specification as well as the claims filed herein.

Example 1. A soil sensor includes a signal generator. The soil sensor further includes a transmitter coupled to the signal generator, the transmitter configured to transmit a signal from the signal generator, the signal having a fixed frequency, the transmitter including a transmit electrode embedded within a first dielectric material. The soil sensor further includes a receiver, the receiver being configured to electrostatically couple to the transmitter through a channel including soil, the receiver including a charge variation (QVAR) electrode embedded within a second dielectric material. The soil sensor further includes a charge variation (QVAR) sensor coupled to the QVAR electrode, the QVAR sensor configured to detect a variation in charge detected at the QVAR electrode in response to the signal from the signal generator and output a digital signal including the charge detected. And the soil sensor further includes a processing circuit coupled to the QVAR sensor and configured to determine a level of moisture in the channel based on the digital signal.

Example 2. The soil sensor of example 1, further includes a power supply to power the processing circuit.

Example 3. The soil sensor of one of examples 1 or 2, further includes a transceiver to transmit the determined level of moisture in the channel, and to receive instructions for operation of the signal generator.

Example 4. The soil sensor of one of examples 1 to 3, where the processing circuit and the signal generator are disposed within a common water-proof casing.

Example 5. The soil sensor of one of examples 1 to 4, where the processing circuit and the signal generator are enclosed in separate water-proof casings and coupled to each other through water-proof cables.

Example 6. The soil sensor of one of examples 1 to 5, where the first dielectric material and the second dielectric material include the same dielectric material.

Example 7. The soil sensor of one of examples 1 to 6, where the first dielectric material and the second dielectric material include polytetrafluoroethylene, polyimide, glass, polyester, or metal oxides.

Example 8. The soil sensor of one of examples 1 to 7, where the first dielectric material and the second dielectric material provide a water-proof seal around the respective transmit and QVAR electrodes.

Example 9. The soil sensor of one of examples 1 to 8, where the receiver and transmitter electrodes include regions of metal on a PCB.

Example 10. The soil sensor of one of examples 1 to 9, further includes a filter to remove noise from the detected signal at the receiver.

Example 11. A soil moisture detection method includes having a transmitter and a receiver of a soil sensor in a patch of soil. The soil moisture detection method further includes transmitting an output signal from a signal generator through the transmitter. The soil moisture detection method further includes detecting the output signal at the receiver. The soil moisture detection method further includes sensing the detected output signal at a charge variation (QVAR) sensor as QVAR signal. And the soil moisture detection method further includes processing the digital signal from the QVAR sensor to obtain a moisture content of the patch of soil.

Example 12. The soil moisture detection method of example 11, further includes filtering the digital signal using a filter.

Example 13. The soil moisture detection method of one of examples 11 or 12, where the filtering includes removing noise generated from transmission of power.

Example 14. The soil moisture detection method of one of examples 11 to 13, further includes transmitting the moisture content of the patch of soil.

Example 15. The soil moisture detection method of one of examples 11 to 14, where the transmitter includes a transmit electrode embedded within a first dielectric material, and where the receiver includes a charge variation (QVAR) electrode embedded within a second dielectric material.

Example 16. The soil moisture detection method of one of examples 11 to 15, where the first dielectric material and the second dielectric material provide a water-proof seal around the respective transmit and QVAR electrodes.

Example 17. The soil moisture detection method of one of examples 11 to 16, where the first dielectric material and the second dielectric material include polytetrafluoroethylene, polyimide, glass, polyester, or metal oxides.

Example 18. A soil sensor calibration method includes placing a transmitter and a receiver of a soil sensor in a first patch of soil. The soil sensor calibration method further includes generating a first soil moisture measurement using the soil sensor. The soil sensor calibration method further includes after generating the first soil moisture measurement, adding a known volume of water to the patch of soil. The soil sensor calibration method further includes after adding the water, generating a second soil moisture measurement using the soil sensor. And the soil sensor calibration method further includes determining a moisture content calibration table for the soil based on the first and the second moisture measurements.

Example 19. The method of example 18, further includes placing a transmitter and a receiver of a soil sensor in a second patch of soil. The soil sensor calibration method further includes generating a third soil moisture measurement using the soil sensor. And the soil sensor calibration method further includes determining a moisture content of the second patch based on the third soil moisture measurement and the moisture content calibration table.

Example 20. The method of one of examples 18 or 19, where the first patch and the second patch are from a same sample of the soil.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A soil sensor comprising:

a signal generator;

a transmitter coupled to the signal generator, the transmitter configured to transmit a signal from the signal generator, the signal having a fixed frequency, the transmitter comprising a transmit electrode embedded within a first dielectric material;

a receiver, the receiver being configured to electrostatically couple to the transmitter through a channel comprising soil, the receiver comprising a charge variation (QVAR) electrode embedded within a second dielectric material;

a charge variation (QVAR) sensor comprising differential inputs, one of the differential inputs being coupled to the QVAR electrode, the QVAR sensor configured to detect a variation in charge between the differential inputs detected at the QVAR electrode in response to the signal from the signal generator polarizing water molecules disposed in the soil and output a digital signal comprising the variation in charge detected; and a processing circuit coupled to the QVAR sensor and configured to determine a level of moisture in the channel based on the digital signal.

2. The soil sensor of claim 1, further comprising a power supply to power the processing circuit.

3. The soil sensor of claim 1, further comprising a transceiver to transmit the determined level of moisture in the channel, and to receive instructions for operation of the signal generator.

4. The soil sensor of claim 1, wherein the processing circuit and the signal generator are disposed within a common water-proof casing.

5. The soil sensor of claim 1, wherein the processing circuit and the signal generator are enclosed in separate water-proof casings and coupled to each other through water-proof cables.

6. The soil sensor of claim 1, wherein the first dielectric material and the second dielectric material comprise the same dielectric material.

7. The soil sensor of claim 6, wherein the first dielectric material and the second dielectric material comprise polytetrafluoroethylene, polyimide, glass, polyester, or metal oxides.

8. The soil sensor of claim 1, wherein the first dielectric material and the second dielectric material provide a water-proof seal around the respective transmit and QVAR electrodes.

9. The soil sensor of claim 1, wherein the QVAR and transmit electrodes comprise regions of metal on a PCB.

10. The soil sensor of claim 1, further comprising a filter to remove noise from the detected signal at the receiver.

11. A soil moisture detection method comprising:

having a transmitter and a receiver of a soil sensor in a patch of soil;

transmitting an output signal from a signal generator through the transmitter;

detecting the output signal at the receiver;

sensing the detected output signal at a charge variation (QVAR) sensor as a digital signal comprising a variation in charge detected between differential inputs of the QVAR sensor, one of the differential inputs being coupled to the receiver, the digital signal being different from the output signal in response to the output signal polarizing water molecules in the patch of soil; and processing the digital signal from the QVAR sensor to obtain a moisture content of the patch of soil.

12. The soil moisture detection method of claim 11, further comprising filtering the digital signal using a filter.

13. The soil moisture detection method of claim 12, wherein the filtering comprises removing noise generated from transmission of power.

14. The soil moisture detection method of claim 11, further comprising transmitting the moisture content of the patch of soil.

15. The soil moisture detection method of claim 11, wherein the transmitter comprises a transmit electrode embedded within a first dielectric material; and wherein the receiver comprises a charge variation (QVAR) electrode embedded within a second dielectric material.

16. The soil moisture detection method of claim 15, wherein the first dielectric material and the second dielectric material provide a water-proof seal around the respective transmit and QVAR electrodes.

17. The soil moisture detection method of claim 15, wherein the first dielectric material and the second dielectric material comprise polytetrafluoroethylene, polyimide, glass, polyester, or metal oxides.

18. A soil sensor calibration method comprising:

placing a transmitter and a receiver of a soil sensor in a first patch of soil;

generating a first soil moisture measurement using a charge variation (QVAR) sensor of the soil sensor, the QVAR sensor comprising differential inputs coupled to an analog front end (AFE) circuit, and a processing unit, one of the differential inputs being coupled to the receiver, the first soil moisture measurement comprising a first variation in charge between the differential inputs of the QVAR sensor;

after generating the first soil moisture measurement, adding a known volume of water to the first patch of soil;

after adding the water, generating a second soil moisture measurement using the QVAR sensor of the soil sensor, the second soil moisture measurement comprising a second variation in charge between the differential inputs of the QVAR sensor; and determining a moisture content calibration table for the first patch of soil based on the first and the second soil moisture measurements.

19. The method of claim 18, further comprising:

placing the transmitter and the receiver of the soil sensor in a second patch of soil;

generating a third soil moisture measurement using the QVAR sensor of the soil sensor, the third soil moisture measurement comprising a third variation in charge between the differential inputs of the QVAR sensor; and determining a moisture content of the second patch of soil based on the third soil moisture measurement and the moisture content calibration table.

20. The method of claim 19, wherein the first patch and the second patch are from a same sample of the soil.

* * * * *